(12) United States Patent
Grüner (10) Patent No.: US 11,660,155 B2
(45) Date of Patent: May 30, 2023

(54) MEDICAL INSTRUMENT (71) Applicant: KARL STORZ SE & Co. KG, Tuttlingen (DE)

(72) Inventor: Sven Grüner, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 400 days.

(21) Appl. No.: 16/935,628

(22) Filed: Jul. 22, 2020

(65) Prior Publication Data
US 2021/0038331 A1 Feb. 11, 2021

(30) Foreign Application Priority Data
Aug. 5, 2019 (DE) ...................... 10 2019 121 092.5

(51) Int. Cl.
*A61B 34/30* (2016.01)
*A61B 34/00* (2016.01)
*B25J 9/10* (2006.01)

(52) U.S. Cl.
CPC .............. *A61B 34/71* (2016.02); *A61B 34/30* (2016.02); *B25J 9/1035* (2013.01); *A61B 2034/301* (2016.02)

(58) Field of Classification Search
CPC . A61B 19/201; A61B 19/203; A61B 19/5244; A61B 34/00; A61B 34/30; A61B 34/71; A61B 2034/301
See application file for complete search history.

(56) References Cited

U.S. PATENT DOCUMENTS

| 5,454,827 | A | 10/1995 | Aust et al. |
| 6,331,181 | B1 * | 12/2001 | Tierney ................. A61B 34/37 606/130 |
| 7,828,808 | B2 | 11/2010 | Hinman et al. |
| 10,259,129 | B2 | 4/2019 | Armand et al. |

(Continued)

FOREIGN PATENT DOCUMENTS

JP 2009148557 A 7/2009

OTHER PUBLICATIONS

Search Report, EP 20187715.6, dated Nov. 12, 2020 (7 pp.).

(Continued)

*Primary Examiner* — Vi X Nguyen
(74) *Attorney, Agent, or Firm* — Eversheds Sutherland (US) LLP (57) ABSTRACT

This application is directed to a medical instrument with a hollow shaft, an actuating unit at the proximal end and an instrument tip with an instrument at the distal end, wherein the instrument can be actuated via an actuating element in the shaft, the element being in an connection with the actuating unit and the instrument tip being pivotable via a joint mechanism, the joint mechanism having pivoting members connected with a proximal-side drive via steering wires running in the direction of the shaft in such a way that movement of the proximal-side drive causes a corresponding movement of the distal-side pivoting members and a pivoting of the instrument tip and wherein the proximal-side drive includes a spatially adjustable disk on which the steering wires are mounted. In order that the steering wires may be controlled precisely and reproducibly, the drive for the spatially adjustable disk is a motorized drive.

16 Claims, 6 Drawing Sheets

(56) References Cited

U.S. PATENT DOCUMENTS

| | | |
|---|---|---|
| 2005/0273084 A1 | 12/2005 | Hinman et al. |
| 2006/0020287 A1 | 1/2006 | Lee et al. |
| 2014/0257333 A1* | 9/2014 | Blumenkranz ........ A61B 34/74 606/130 |
| 2015/0321343 A1 | 11/2015 | Armand et al. |
| 2015/0352728 A1 | 12/2015 | Wang |
| 2016/0066982 A1 | 3/2016 | Marczyk et al. |

OTHER PUBLICATIONS

JP Office Action, JP 2020-131571, dated Jul. 6, 2021 (in Japanese) (4 pp.).
Search Report, DE 10 2019 121 092.5, dated Jun. 17, 2020 (8 pp.).

\* cited by examiner

MEDICAL INSTRUMENT

TECHNICAL FIELD

The invention relates to a medical instrument with a hollow shaft, an actuating unit arranged at the proximal end of the shaft and an instrument tip with an instrument arranged at the distal end, wherein the instrument can be actuated via an actuating element mounted axially displaceably in the shaft, said element being in an operative connection with the actuating element on the proximal side and the instrument tip being pivotable relative to the longitudinal axis of the shaft via a joint mechanism, the joint mechanism consisting of pivoting members arranged at the distal end of the shaft, which are connected with a proximal-side drive via steering wires running in the longitudinal direction of the shaft in such a way that a movement of the proximal-side drive causes a corresponding relative movement of the distal-side pivoting members and thus a pivoting of the instrument tip as well as a trigger mechanism, with the proximal-side drive comprising a spatially adjustable disk on which the steering wires are mounted.

BACKGROUND OF THE INVENTION

Pivoting members with three, four or more external steering wires/steering cables for bendable medical instruments are known in practice for hand-held and/or robotic instruments. For a sensitive control of the distal end of such a medical instrument, many thin steering wires/steering cables have proven to be more advantageous than a few thicker steering wires/steering cables since, among other things, a more even distribution of force can be achieved in all directions of deflection, and, moreover, thinner steering wires/steering cables allow for more space in the interior for electrical cables and the like.

A generic medical instrument is known, for example, from U.S. Pat. No. 5,454,827. In this known medical instrument, the distal-side pivoting members are coupled via four steering wires to a spatially adjustable disk arranged on the proximal side such that a movement of the spatially adjustable disk causes a corresponding relative movement of the distal-side pivoting members and thus a pivoting of the tool tip, the movement of the spatially adjustable disk being performed manually by using a type of joystick that is directly coupled to the spatially adjustable disk.

The design of the drive for the steering wires as a spatially adjustable disk on which all four steering wires are mounted has the advantage that it enables a spatially compact design, and only one component has to be moved in order to activate all steering wires.

Disadvantages of this known construction are, on the one hand, the use of only a small number of steering wires, namely only four steering wires and, on the other hand, the exclusively manual actuation of the spatially adjustable disk serving as a drive for the steering wires, due to which a sensitive and reproducible adjustment of the distal-side pivoting members is hardly possible.

SUMMARY OF THE INVENTION

Based on this, the object of the invention is to create a medical instrument of the type mentioned at the beginning by means of which any number of steering wires can be controlled precisely and reproducibly.

To achieve this object, the invention is characterized by the fact that the drive for the spatially adjustable disk is designed as a motorized drive.

The motorized drive of the spatially adjustable disk, according to the invention, makes it possible to activate the steering wires for pivoting the distal-side pivoting members or the tool tip precisely, sensitively in the smallest steps and also reproducibly. In addition, the number of steering wires to be used for a motorized drive is irrelevant.

A practical embodiment of the invention proposes that the motorized drive consists of two drive units arranged offset to one another by 180° whose drive shafts lie on a common central axis and the spatially adjustable disk being arranged between the two drive units. By using only two drives, the spatially adjustable disk can be moved in such a way that the tool tip coupled to the steering wires can be pivoted in all spatial directions relative to the longitudinal axis of the shaft. The two drive units are advantageously designed as driven gearwheels, in particular bevel gearwheels.

According to a preferred embodiment of the invention, it is proposed that the spatially adjustable disk is coupled to a third gearwheel which engages with the two driven gearwheels and whose axis of rotation intersects with the central axis of the drive units designed as driven gearwheels. Due to the three intermeshing gearwheels, each movement of the two driven gearwheels is transmitted directly to the third gearwheel coupled to the spatially adjustable disk, which in turn causes a direct actuation of the steering wires.

In order to be able to adjust the spatially adjustable disk in three dimensions despite the rotationally fixed coupling to the third gearwheel, it is proposed, according to a preferred embodiment of the invention, that the spatially adjustable disk is gimbal-mounted on a main shaft running coaxially to the longitudinal axis of the shaft.

To form the gimbal-mounted bearing of the spatially adjustable disk, it is proposed, according to the invention, that the spatially adjustable disk is pivotably mounted on a universal joint disk via two bearing pins which are offset by 180° with the universal joint disk being pivotably mounted on the main shaft via two bearing pins which are offset by 180° and the bearing pins of the spatially adjustable disk and the universal joint disk being arranged offset to one another by 90°. This mounting enables the spatially adjustable disk to be pivoted relative to the longitudinal axis of the shaft about two axes perpendicular to one another; as a result, the tool tip can be pivoted in all spatial directions relative to the longitudinal axis of the shaft via the steering wires on the distal side.

In order to further enable the tool tip to be rotatable about the longitudinal axis of the shaft in addition to pivoting relative to the longitudinal axis of the shaft, the invention proposes that the spatially adjustable disk is rotatably mounted on the third gearwheel around the longitudinal axis of the shaft whereby a twisting of the steering wires is prevented.

According to a practical embodiment of the invention, it is proposed that the spatially adjustable disk be arranged in a steering ring coupled to the third gearwheel such that it does not rotate.

Furthermore, the invention proposes that the spatially adjustable disk is mounted rotatably about the longitudinal axis of the shaft in a bearing ring with the bearing ring being mounted in the steering ring.

Furthermore, the invention proposes that a fourth gearwheel, which is in engagement with the two driven gearwheels, is arranged on the axis of rotation of the third gearwheel such that it is offset from the third gearwheel by 180°. This fourth gearwheel closes the revolving gear chain and thus ensures an even, circumferential, and play-free power distribution.

According to the invention, the spatially adjustable disk is coupled with the third gearwheel in a freely rotatable manner with respect to the fourth gearwheel so that the rotation of the fourth gearwheel about its axis of rotation does not cause the spatially adjustable disk to be rotated.

According to the invention, the steering wires are fixed to the spatially adjustable disk by means of a clamping connection, for example by means of grub screws, which fix the steering wires in a clamped manner in through holes formed in the spatially adjustable disk.

According to a further embodiment of the invention, it is proposed that, on the distal side in front of the spatially adjustable disk, a serrated disk is arranged on the main shaft, which increases the radial distance of the steering wires from the longitudinal axis of the shaft. By increasing the radial distance of the steering wires from the longitudinal axis of the shaft, for example from a diameter of 4 mm to a diameter of 18 mm, not only is the assembly and manufacture of the drive of the steering wires equipped with the spatially adjustable disk simplified but also the adjustment angle of the spatially adjustable disk is reduced in order to achieve a pivoting angle of the tool tip corresponding to the dimension of the diameter increase.

A first embodiment for the arrangement of the drive units for actuating the spatially adjustable disk proposes, according to the invention, that the central axis of the two drive units designed as driven gearwheels is arranged perpendicular to the longitudinal axis of the shaft. This arrangement of the drive units in which the longitudinal axis of the shaft passes between the two drive units has a structure that is particularly easy to manufacture.

With an alternative embodiment for the arrangement of the drive units, the invention proposes that the central axis of the two drive units designed as driven gearwheels coincide with the longitudinal axis of the shaft. This embodiment is characterized by a particularly space-saving, slim design.

Finally, the invention proposes that when the drive units are arranged in the longitudinal direction of the longitudinal axis of the shaft, the two driven gearwheels are designed as hollow gearwheels in order to be able to arrange the actuating element for actuating the tool in the longitudinal direction of the shaft on the one hand and on the other hand feed the steering wires to the spatially adjustable disk.

In order to avoid a collision of the gearwheels with the steering wires and possibly the actuating element when pivoting the third and fourth gearwheel relative to the longitudinal axis of the shaft, the invention furthermore proposes that recesses are formed for the steering wires and the actuating element.

BRIEF DESCRIPTION OF THE DRAWINGS

Further features and advantages of the invention can be obtained from the associated drawings in which two exemplary embodiments of a medical instrument, according to the invention, are only shown by way of example without limiting the invention to these exemplary embodiments. The drawings show the following:

FIG. 4b shows a partially sectioned representation of the view of FIG. 4a;

DETAILED DESCRIPTION

Figure 1:
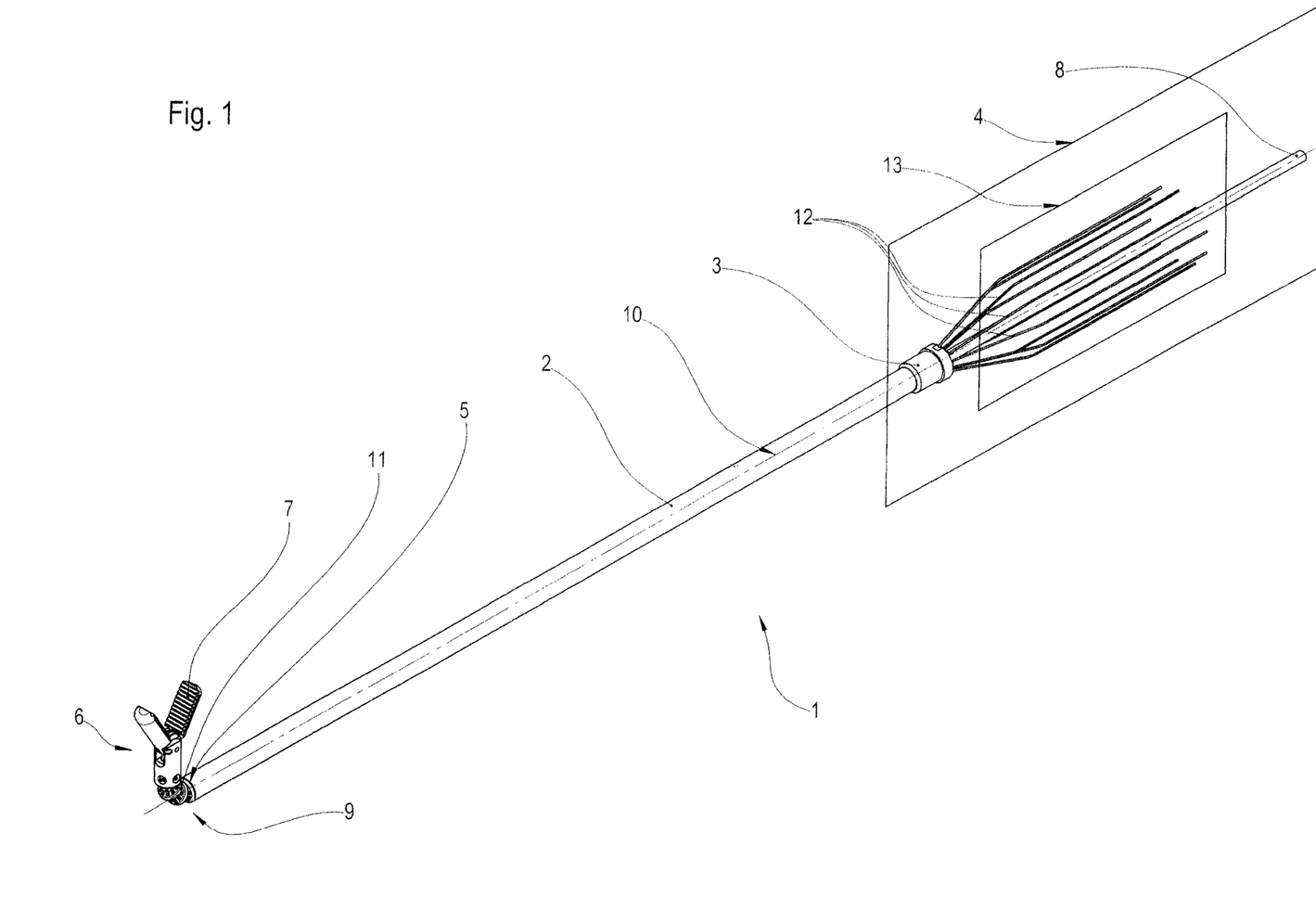
FIG. 1 shows a schematic perspective side view of a medical instrument according to the invention.
Figure 2:
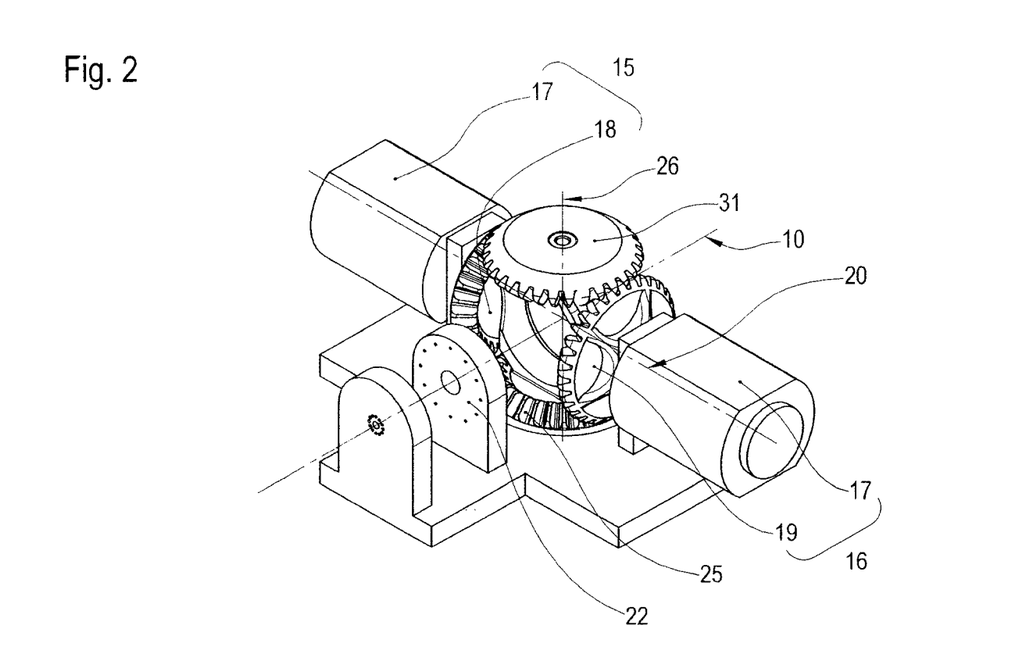
FIG. 2 shows an enlarged schematic representation of a first embodiment of the drive according to FIG. 1.

FIG. 1 schematically shows a medical instrument 1 with a hollow shaft 2, an actuating unit 4 arranged at the proximal end 3 of the shaft 2, which is only shown schematically, and an instrument tip 6 with an instrument 7, which is arranged at the distal end 5 of the shaft 2, wherein the instrument 7 can be actuated via an actuating element 8 which is mounted axially displaceably in the shaft 2 and which is operatively connected to the actuating unit 4 on the proximal side.

The actuating unit 4 may be a manually operable handle or also a structural unit designed for robotic use, i.e., it may also be operable without any manual intervention.

The instrument 7 of the instrument tip 6 may, for example, be a tool that is provided with jaw parts, as shown in FIG. 1, or an endoscope, an applicator or the like.

The instrument tip 6 can be pivoted relative to the longitudinal axis 10 of the shaft 2 by means of a joint mechanism 9, the joint mechanism 9 consisting of pivoting members 11 arranged at the distal end 5 of the shaft 2 and having steering wires 12 running in the longitudinal direction of the shaft 2 that are connected to a drive 13 arranged at the proximal end 3 of the shaft 2 such that a movement of the proximal-side drive 13 causes a corresponding relative movement of the distal-side pivoting members 11 and thus a pivoting of the instrument tip 6.

Even if only the term steering wires 14 is used above and below, steering cables may also be used with respect to function, which is why the term steering wires 14 used is to be read and understood synonymously as a steering cable.

The axially displaceable actuating element 8 mounted in the shaft 2 for actuating the instrument 7, for example consisting of two jaw parts, is designed as a pull/push rod in the illustrated embodiments.

The drive 13 for the steering wires 12 is designed as a motorized drive 13 in the medical instrument 1 shown in the figures and described below.

The centerpiece of the drive 13 is a spatially adjustable disk 14 (FIGS. 4-6) on which the steering wires 12 are mounted such that a displacement of the spatially adjustable disk 14 via the steering wires 12 mounted on the spatially adjustable disk 14 causes the instrument tip 6 to pivot. This spatially adjustable disk 14 is displaceable via the motorized drive 13.

By using a motorized drive 13 for the spatially adjustable disk 14, it is possible to control the steering wires 12 for pivoting the distal-side pivoting members 11 or the instrument tip 6 precisely, sensitively in the smallest steps and also reproducibly. In addition, the number of steering wires 12 to be used for a motorized drive 13 is irrelevant.

The motorized drive 13 in turn consists of two drive units 15 and 16 arranged offset to one another by 180° with their drive shafts lying on a common central axis 20 and the spatially adjustable disk 14 being arranged between the two drive units 15 and 16. The drive units 15 and 16 themselves are designed as gearwheels 18 and 19, preferably bevel gears, which are driven by motors 17.

In the first embodiments of the motorized drive 13 shown in FIGS. 2 and 4 to 6, the central axis 20 of the two drive units 15 and 16 is arranged perpendicular to the longitudinal axis 10 of the shaft 2 and crosses the longitudinal axis 10 of the shaft 2.

Figure 3:
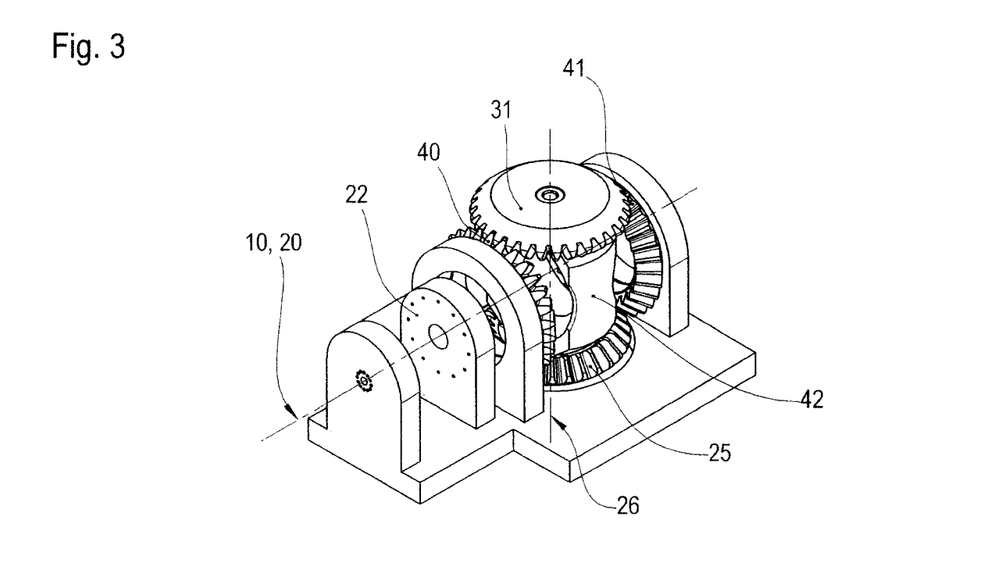
FIG. 3 shows an enlarged schematic representation of a second embodiment of the drive according to FIG. 1.

According to the alternative second embodiment shown in FIG. 3, the central axis 20 of the two drive units 15 and 16 coincides with the longitudinal axis 10 of the shaft 2.

The structure of the spatially adjustable disk 14 and its mounting described below are identical in both embodiments of the motorized drive 13.

The construction and operation of the motorized drive 13 and in particular the spatially adjustable disk 14 which can be actuated via the drive units 15 and 16 will be described below with reference to FIGS. 4, 5 and 6.

As can be seen from the figures, a hollow main shaft 21, which is coaxially arranged with the longitudinal axis 10 of the shaft 2, which is rotatable about the longitudinal axis 10 of the shaft 2 and extends beyond the proximal end 3 of the shaft 2 to the region of the motorized drive 13 extends. The actuating element 8 for actuating the instrument 7 is mounted axially displaceably within this hollow main shaft 21.

The steering wires 12 emerging from the shaft 2 at the proximal end 3 of the shaft 2 are fanned out via a serrated lock washer 22 arranged on the main shaft 21 so that the radial distance of the steering wires 12 from the longitudinal axis 10 of the shaft 2 is increased. While the diameter of the bundle of steering wires 12 coaxially surrounding the longitudinal axis 10 of the shaft 2 within the shaft 2 is, for example, 4 mm, the diameter of the bundle formed by the steering wires behind the serrated washer 22 is, for example, 18 mm. In the exemplary embodiment shown, the bundle consists of ten individual steering wires 12.

On the proximal side behind the serrated lock washer 22, the steering wires 12 which run parallel to the longitudinal axis 10 of the shaft 2 are fed to the spatially adjustable washer 14. To fix the steering wires 12 to the spatially adjustable disk 14, through holes 23 are formed for each steering wire 12 in the spatially adjustable disk 14 with the steering wires 12 being fixable within the through holes 23 via grub screws 24 and non-positively connected to the spatially adjustable disk 14.

The driven gearwheels 18 and 19 are in turn coupled to a third gearwheel 25 which engages with the two driven gearwheels 18 and 19 and whose axis of rotation 26 intersects with the central axis 20 of the drive units 15 and 16 designed as driven gearwheels 18 and 19 and the longitudinal axis 10 of the shaft 2 at the intersection S. The third gearwheel 25 is also preferably designed as a bevel gear.

Due to the three intermeshing gearwheels 18, 19 and 25, each movement of the two driven gearwheels 18 and 19 is transmitted directly to the spatially adjustable disk 14 coupled to the third gearwheel 25, which in turn causes a direct actuation of the steering wires 12.

To form a gimbal-mounted bearing of the spatially adjustable disk 14 on the main shaft 21, the spatially adjustable disk 14 is pivotably mounted on a universal joint disk 28 via two bearing pins 27 which are offset by 180° with the universal joint disk 28 being pivotably mounted on the main shaft 21 via two bearing pins 29 which are offset by 180°. For reasons of better clarity, only one bearing pin 27 and one bearing pin 29 are shown in FIGS. 4-6.

The bearing pins 27 of the spatially adjustable disk 14 and the bearing pins 29 of the universal joint disk 28 are offset from one another by 90°. This mounting enables the spatially adjustable disk 14 to be pivoted relative to the longitudinal axis 10 of the shaft 2 about two axes perpendicular to one another; as a result, the instrument tip 6 can be pivoted in all spatial directions relative to the longitudinal axis 10 of the shaft 2 via the steering wires 12 on the distal side.

Figure 4A:
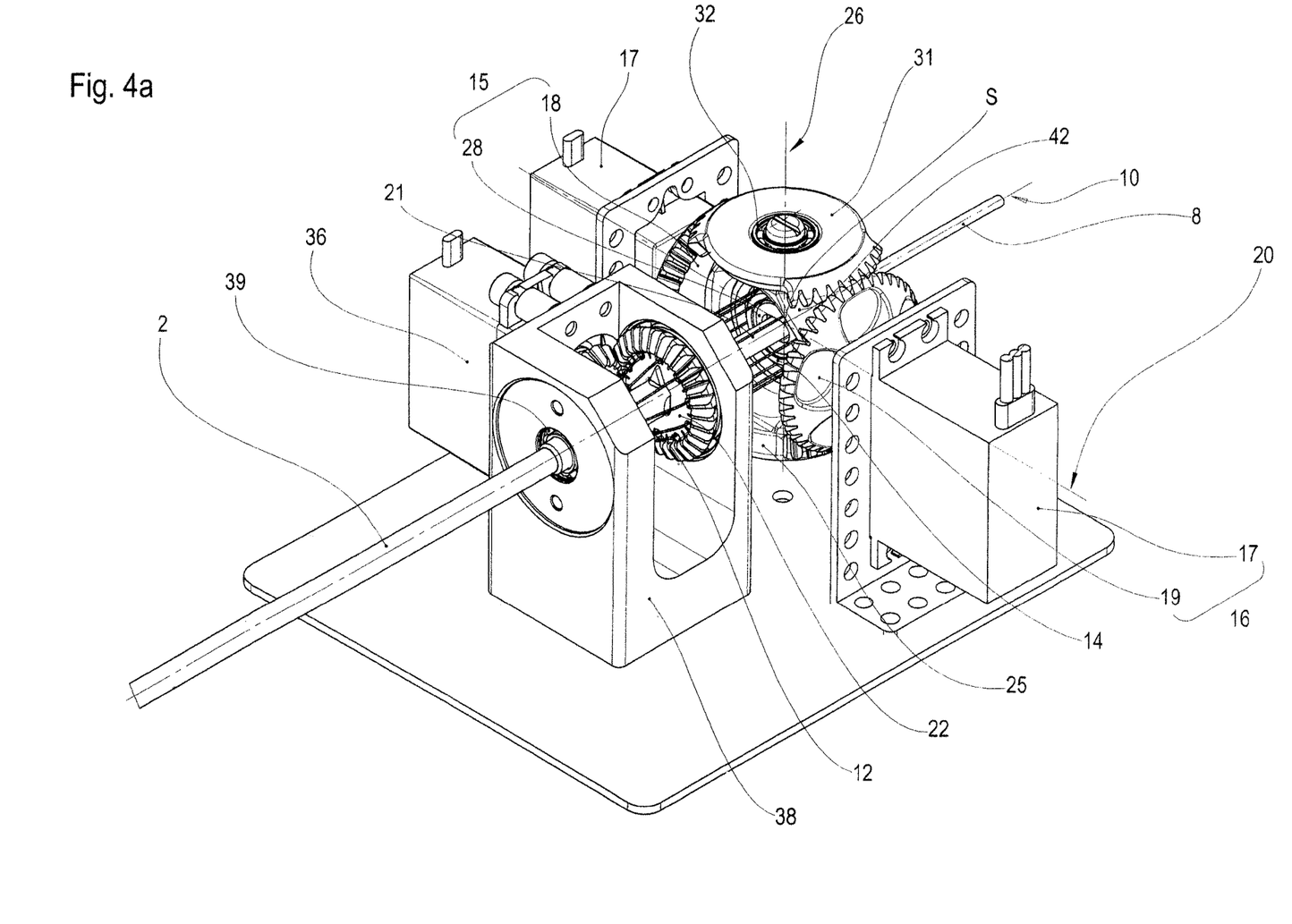
FIG. 4a shows an enlarged perspective detailed view of a drive according to FIG. 2, showing the drive in a neutral starting position.
Figure 4B:
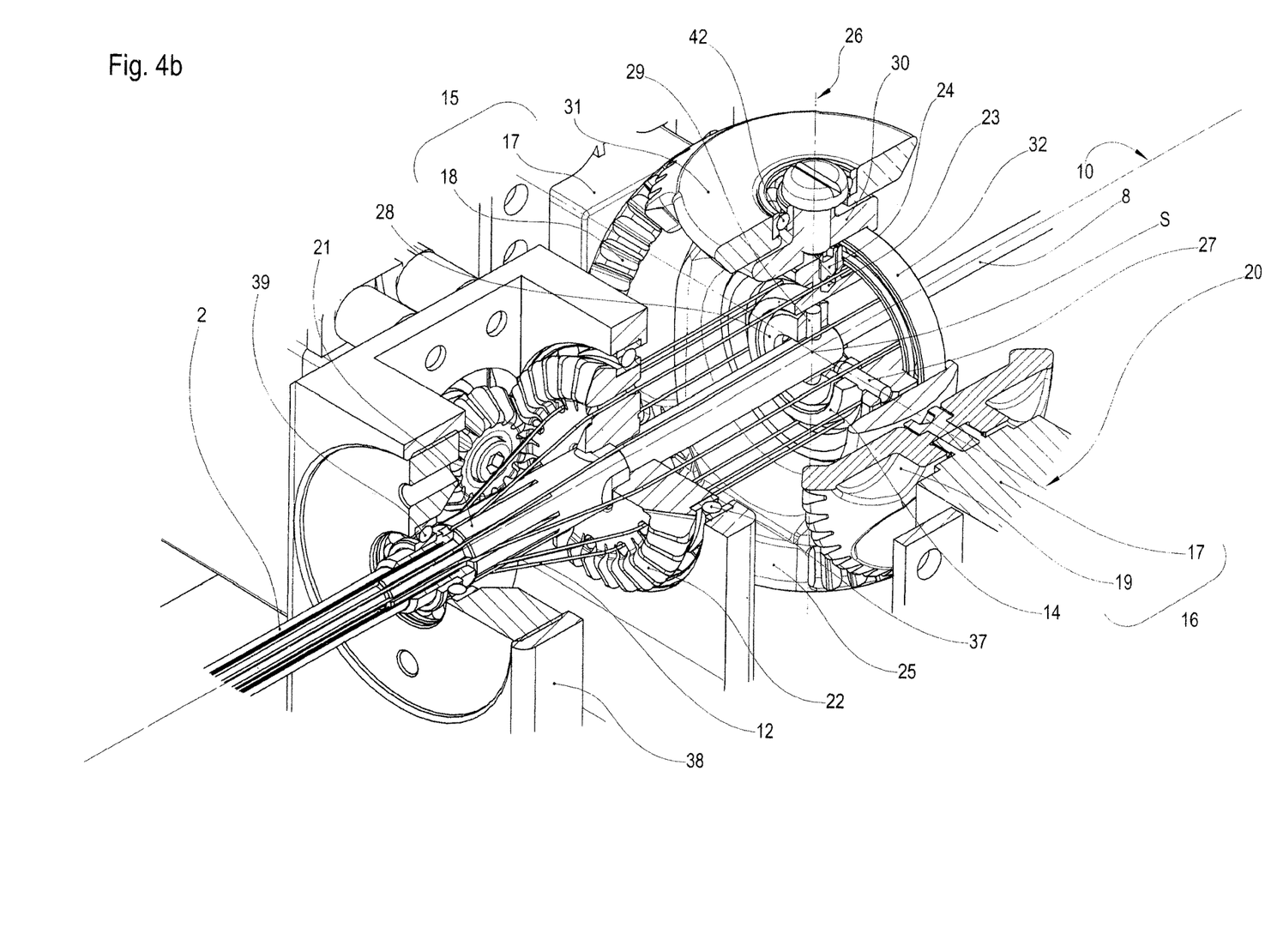
Figure 5:
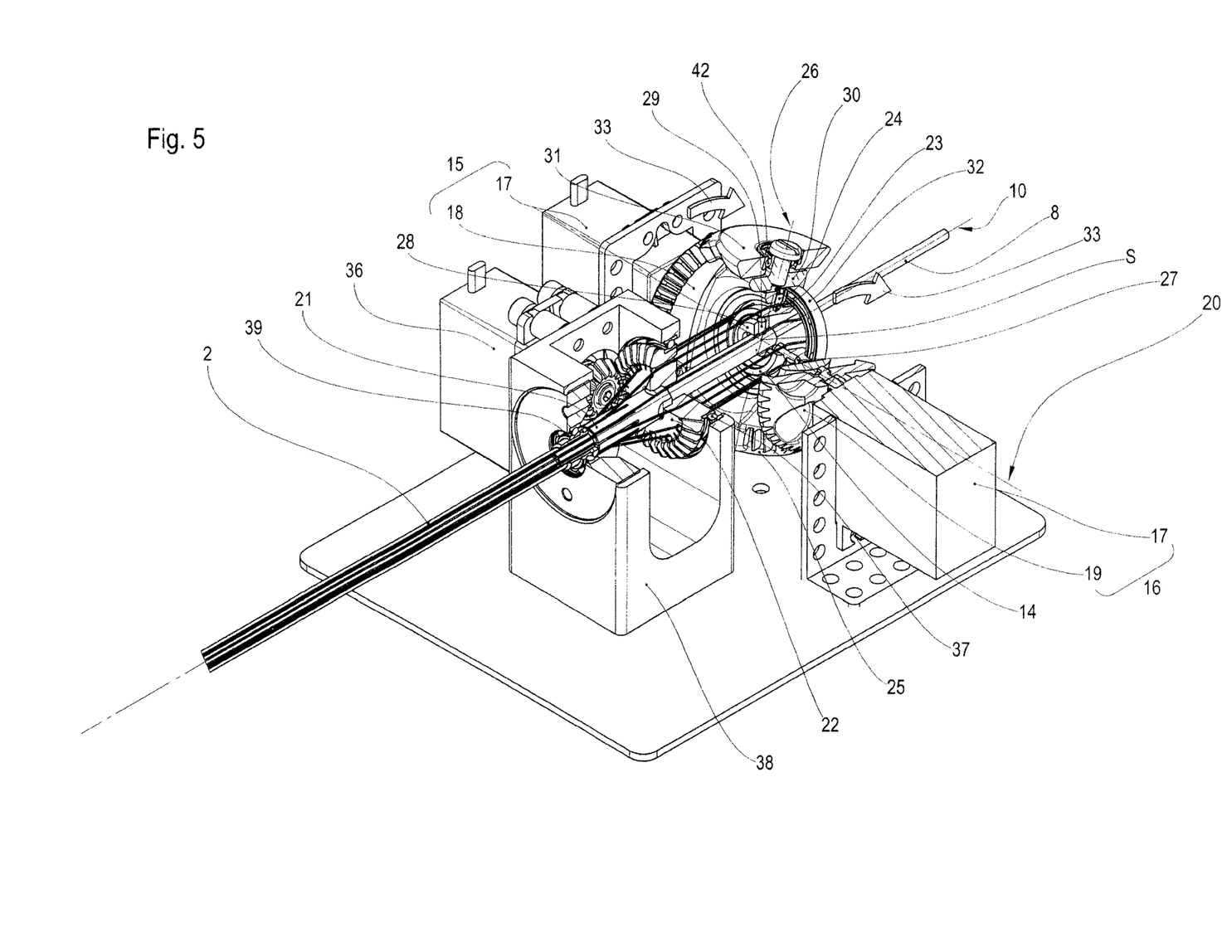
FIG. 5 shows a view of FIG. 4 but with the drive in a first working position and FIG. 6 shows a view of FIG. 4 but with the drive in a second working position.
Figure 6:
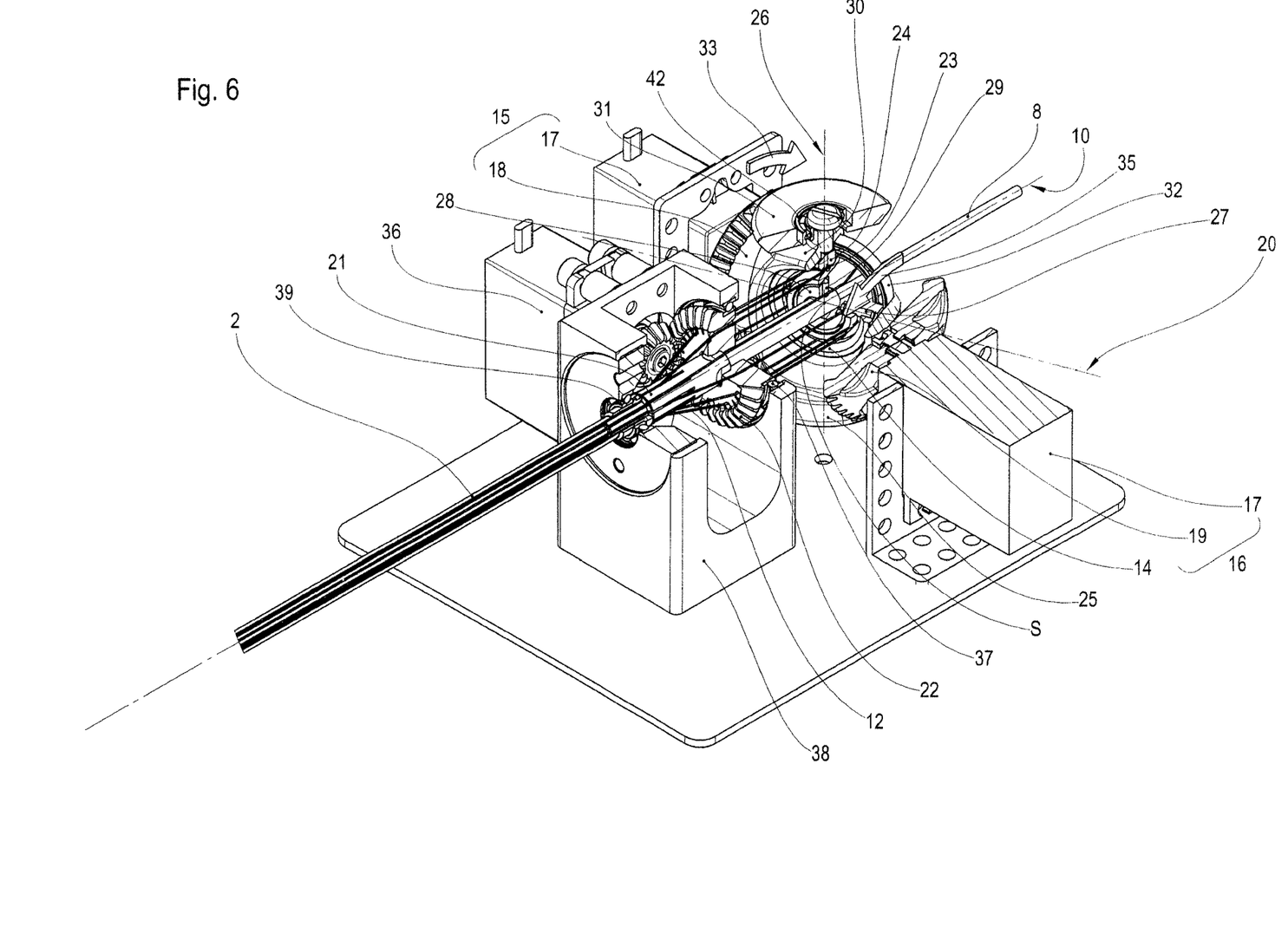

As can be seen from FIGS. 4-6, the spatially adjustable disk 14 is mounted in a steering ring 30 which is non-rotatably coupled to the third gearwheel 25.

In order to close the toothed chain formed by the gearwheels 18, 19 and 25 to form a closed toothed ring, which ensures a uniform circumferential distribution of force, a fourth toothed gearwheel 31 is arranged on the axis of rotation 26 of the third toothed gearwheel 25 offset from the third toothed gearwheel 25 by 180°, which is in engagement with the two driven gearwheels 18 and 19 with the fourth gearwheel 31 also preferably being designed as a bevel gear.

The spatially adjustable disk 14 is mounted via a bearing ring 32 in the steering ring 30, which is non-rotatably coupled to the third gearwheel 25, in order to enable the spatially adjustable disk 14 to rotate about the longitudinal axis 10 of the shaft 2.

The steering ring 30, which is non-rotatably coupled to the third gearwheel 25, can be freely rotated relative to the fourth gearwheel 31 via a bearing ring 42 so that the rotation of the fourth gearwheel 31 about its axis of rotation 26 does not cause the steering ring 30 and the spatially adjustable disk 14 to rotate.

The described gimbal mounting of the spatially adjustable disk 14 on the main shaft 21 makes it possible to displace the spatially adjustable disk 14 three-dimensionally relative to the longitudinal axis 10 of the shaft 2 as shown in FIGS. 5 and 6.

If starting from the neutral starting position shown in FIG. 4 in which the spatially adjustable disk 14 is oriented perpendicular to the longitudinal axis 10 of the shaft 2, the driven gearwheels 18 and 19 are driven by the motors 17 such that the gearwheels 18 and 19 turn in the same direction, for example in the direction of the arrows 33 in FIG. 5 to the right (or counter to the direction of the arrows 33 to the left); this rotation of the driven gearwheels 18 and 19 causes, due to the meshing engagement with the third gearwheel 25 and the fourth gearwheel 31, a tilting of the structural unit formed from the third gearwheel 25, the spatially adjustable disk 14 coupled to the third gearwheel 25, and the fourth gearwheel 31 around the central axis 20 of the driven gears 18 and 19 as shown in FIG. 5.

The bearing pins 27, which are aligned with the central axis 20 of the driven gearwheels 18 and 19 and via which the spatially adjustable disk 14 is pivotably mounted on the universal joint disk 28, enable the spatially adjustable disk 14 to tilt relative to the universal joint disk 28.

This tilting of the spatially adjustable disk 14 about the central axis 20 relative to the longitudinal axis 10 of the shaft 2 causes, via the steering wires 12, the instrument tip 6 to be pivoted on the distal side in the same way relative to the longitudinal axis 10 of the shaft 2.

If starting from the neutral starting position shown in FIG. 4 in which the spatially adjustable disk 14 is oriented perpendicular to the longitudinal axis 10 of the shaft 2, the driven gearwheels 18 and 19 are driven by the motors 17 such that the gearwheels 18 and 19 rotate in opposite directions, for example, the gearwheel 18 in the direction of the arrow 34 in FIG. 6 to the right and the gearwheel 19 in the direction of the arrow 35 in FIG. 6 to the left (or vice versa); this rotation of the driven gearwheels 18 and 19 causes, due to the meshing engagement with the third gearwheel 25, a rotation of the assembly formed from the third gearwheel 25 and the spatially adjustable disk 14 coupled to the third gearwheel 25 about the axis of rotation 26 of the third gearwheel 25 as shown in FIG. 6.

The bearing pins 29, which are aligned with the axis of rotation 26 of the third gearwheel 25, via which the universal joint disk 28 is pivotably mounted on the main shaft 21, together with the free rotatability of the spatially adjustable disk 14 relative to the fourth gearwheel 31 allow this rotation of the universal joint disk 28 relative to the main shaft 21 due to the bearing ring 32.

This rotation of the spatially adjustable disk 14 about the axis of rotation 26 relative to the longitudinal axis 10 of the shaft 2 causes, via the steering wires 12, the instrument tip 6 to be pivoted relative to the longitudinal axis 10 of the shaft 2 on the distal side in the same way.

In addition to the displacements of the spatially adjustable disk 14 shown in FIGS. 5 and 6, it is, of course, also possible to superimpose the movements shown so that, for example, the spatially adjustable disk tilts about the central axis 20 and at the same time also rotates about the axis of rotation 26. This combination of the two movement sequences due to the individually controllable motors 17 of the drive 13 makes it possible to adjust the spatially adjustable disk 14 three-dimensionally relative to the longitudinal axis 10 of the shaft 2, which results in a spatial displacement of the instrument tip 6 due to the coupling via the steering wires 12.

The enlargement of the radial distance of the steering wires 12 from the longitudinal axis 10 of the shaft 2 achieved by the serrated lock washer 22 not only simplifies the assembly and manufacture of the drive 13 of the steering wires 14 equipped with the spatially adjustable disk 14 but also proportionally reduces the required adjustment angle of the spatially adjustable disk 14 in order to achieve a desired high pivoting angle of the instrument tip 6.

If, for example, the diameter of the bundle formed by the steering wires 12 is increased from 4 mm inside the shaft 2 to 18 mm behind the serrated lock washer 22, i.e. 4.5 times, the adjustment angle of the spatially adjustable disk 14 is reduced by 4.5 times the pivoting angle of the instrument tip 6 that can be achieved at the distal end. In order to angle the instrument tip 6 by 90°, it is therefore only necessary to pivot the spatially adjustable disk 14 by 20°.

In order to set the main shaft 12 in rotation about the longitudinal axis 10 of the shaft 2, as a result of which the instrument tip 6 coupled distally to the main shaft 21 also rotates about the longitudinal axis 10 of the shaft 2, the serrated lock washer 22, which is non-rotatably arranged on the main shaft 21, is designed as a gearwheel, which can be driven by a motor 36, and is rotatably mounted in a bearing block 38 of the actuating unit 4 via a bearing ring 37 in the embodiment of the medical instrument 1 shown in FIGS. 4-6. A further bearing ring 39 arranged distally in front of the serrated lock washer 22 ensures a stable guidance of the main shaft 21.

A rotation of the main shaft 21 about the longitudinal axis 10 of the shaft 2 is transmitted to the spatially adjustable disk 14 via the universal joint disk 28, which is non-rotatably mounted on the main shaft 21 and the bearing pins 27. In the event that the spatially adjustable disk 14 is tilted and/or rotated about the longitudinal axis 10 of the shaft 2 relative to the longitudinal axis 10 of the shaft 2 during the rotation of the main shaft 21, the steering wires 12 fixed on the spatially adjustable disk 14 pass through different control positions, but the distal angling of the instrument tip 6 remains spatially the same despite the rotation of the instrument tip 6 about the longitudinal axis 10 of the shaft 2.

In the alternative arrangement of the drive units 15 and 16 shown in FIG. 3, the two driven toothed gearwheels are designed as hollow gearwheels 40 and 41 in the longitudinal direction of the longitudinal axis 10 of the shaft 2 so as to, on the one hand, be able to arrange the actuating element 8 for actuating the instrument 7 in the longitudinal direction 10 of the shaft 2 and, on the other hand, be able to feed the steering wires 12 of the spatially adjustable disk 14. In this design, the hollow gearwheels 40 and 41 are driven via side gearwheels, which are not shown.

A medical instrument 1 designed as described above is characterized in that many thin steering wires 12 can be used to control the pivotable instrument tip 6 and this control is sensitive, exact and reproducible due to the motorized drive 13 for the spatially adjustable disk 14 on which the steering wires 12 are mounted on the proximal side.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS

1 Medical instrument
2 Shaft
3 Proximal end (shaft)
4 Actuating unit
5 Distal end (shaft)
6 Instrument tip
7 Instrument
8 Actuating element
9 Joint mechanism
10 Longitudinal axis
11 Pivoting member
12 Steering wire
13 Drive
14 Disk (spatially adjustable)
15 Drive unit
16 Drive unit
17 Motor
18 Gearwheel (driven)
19 Gearwheel (driven)
20 Central axis
21 Main shaft
22 Serrated lock washer
23 Through hole
24 Grub screw
25 Third gearwheel
26 Axis of rotation
27 Bearing pin
28 Universal joint disk
29 Bearing pin
30 Steering ring
31 Fourth gearwheel
32 Bearing ring
33 Arrow
34 Arrow
35 Arrow
36 Motor
37 Bearing ring
38 Bearing block
39 Bearing ring
40 Hollow gearwheel
41 Hollow gearwheel 42 Bearing ring
S Intersection

I claim:

1. A medical instrument with a hollow shaft, an actuating unit arranged at the proximal end of the shaft and an instrument tip with an instrument arranged at the distal end of the shaft, wherein the instrument can be actuated via an actuating element mounted axially displaceably in the shaft, the actuating element being in an operative connection with the actuating unit on the proximal side and the instrument tip being pivotable relative to the longitudinal axis of the shaft via a joint mechanism, the joint mechanism having pivoting members arranged on the distal end of the shaft, which are connected with a proximal-side drive via steering wires running in the longitudinal direction of the shaft in such a way that a movement of the proximal-side drive causes a corresponding relative movement of the distal-side pivoting members and thus a pivoting of the instrument tip and wherein the proximal-side drive comprises a spatially adjustable disk on which the steering wires are mounted, characterized in that:
the proximal-side drive for the spatially adjustable disk comprises a motorized drive; and
the two drive units each comprises drive shafts which lie on a common central axis and wherein the spatially adjustable disk is arranged between the two drive units.

2. The medical instrument according to claim 1, characterized in that the drive units are designed as driven gearwheels.

3. The medical instrument according to claim 2, characterized in that the spatially adjustable disk is gimbal-mounted on a main shaft running coaxially to the longitudinal axis of the shaft.

4. The medical instrument according to claim 3, characterized in that the spatially adjustable disk is pivotably mounted on a universal joint disk by means of two bearing pins which are offset by 180°, wherein the universal joint disk is pivotably mounted on the main shaft by means of two bearing pins offset from each other by 180°, and the bearing pins of the spatially adjustable disk and the universal joint disk are arranged offset from each other by 90°.

5. The medical instrument according to claim 4, characterized in that a serrated lock washer is arranged on the main shaft on the distal side in front of the spatially adjustable disk, which increases the radial distance of the steering wires from the longitudinal axis of the shaft.

6. The medical instrument according to claim 3, characterized in that the spatially adjustable disk about the longitudinal axis of the shaft is rotatably mounted on the third gearwheel.

7. The medical instrument according to claim 6, characterized in that the spatially adjustable disk is arranged in a steering ring which is coupled to the third gearwheel in a rotationally fixed manner.

8. The medical instrument according to claim 7, characterized in that the spatially adjustable disk about the longitudinal axis of the shaft is rotatably mounted in a bearing ring with the bearing ring being mounted in the steering ring.

9. The medical instrument according to claim 2, characterized in that the central axis of the two drive units designed as driven gearwheels is arranged perpendicular to the longitudinal axis of the shaft.

10. The medical instrument according to claim 2, characterized in that the central axis of the two drive units designed as driven gearwheels coincides with the longitudinal axis of the shaft.

11. The medical instrument according to claim 10, characterized in that the two driven gearwheels are designed as hollow gearwheels.

12. The medical instrument according to claim 1, characterized in that the spatially adjustable disk is coupled to a third gearwheel which engages with the two driven gearwheels and whose axis of rotation intersects with the central axis of the drive units designed as driven gearwheels.

13. The medical instrument according to claim 12, characterized in that a fourth gearwheel is arranged on the axis of rotation of the third gearwheel offset from the third gearwheel by 180°, which is in engagement with the two driven gearwheels.

14. The medical instrument according to claim 13, characterized in that the spatially adjustable disk is coupled to the third gearwheel via a bearing ring in a freely rotatable manner with respect to the fourth gearwheel.

15. The medical instrument according to claim 13, characterized in that recesses for the steering wires and the actuating element are formed in the ring gears of the third gearwheel and the fourth gearwheel.

16. Medical A medical instrument with a hollow shaft, an actuating unit arranged at the proximal end of the shaft and an instrument tip with an instrument arranged at the distal end of the shaft, wherein the instrument can be actuated via an actuating element mounted axially displaceably in the shaft, the actuating element being in an operative connection with the actuating unit on the proximal side and the instrument tip being pivotable relative to the longitudinal axis of the shaft via a joint mechanism, the joint mechanism having pivoting members arranged on the distal end of the shaft, which are connected with a proximal-side drive via steering wires running in the longitudinal direction of the shaft in such a way that a movement of the proximal-side drive causes a corresponding relative movement of the distal-side pivoting members and thus a pivoting of the instrument tip and wherein the proximal-side drive comprises a spatially adjustable disk on which the steering wires are mounted, characterized in that:
the proximal-side drive for the spatially adjustable disk comprises a motorized drive; and
that the steering wires can be fixed on the spatially adjustable disk by means of a clamping connection.

* * * * *